US00PP19888P2

(12) United States Plant Patent
Akai

(10) Patent No.: US PP19,888 P2
(45) Date of Patent: Apr. 7, 2009

(54) ***EVOLVULUS* PLANT NAMED 'BURUSIERU'**

(50) Latin Name: *Evolvulus pilosus*
Varietal Denomination: BURUSIERU

(76) Inventor: Nobutaka Akai, 4542-4 Ooaza Uriuno, Miyazaki City, Miyazaki (JP), 880-4400

( * ) Notice: Subject to any disclaimer, the term of this patent is extended or adjusted under 35 U.S.C. 154(b) by 0 days.

(21) Appl. No.: 11/978,250

(22) Filed: Oct. 29, 2007

(51) Int. Cl.
*A01H 5/00* (2006.01)

(52) U.S. Cl. ..... Plt./263.1
(58) Field of Classification Search ..... Plt./263.1
See application file for complete search history.

*Primary Examiner*—Annette H Para

(57) ABSTRACT

A new and distinct *Evolvulus* cultivar named 'BURUSIERU' is disclosed, characterized by a shorter, compact plant habit, prolific branching and more linear foliage. The new variety is an *Evolvulus,* and naturally blooms from early Spring through late Summer.

1 Drawing Sheet

Figure 1:
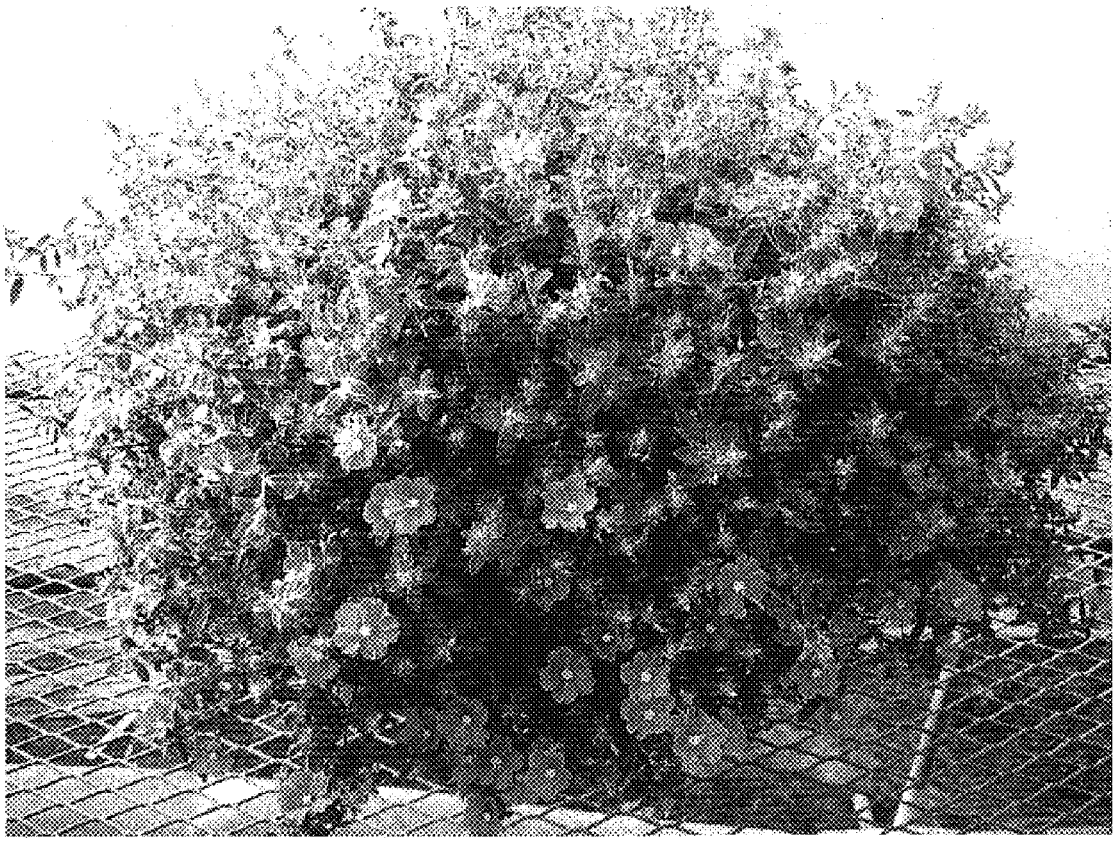

Latin name of the genus and species: *Evolvulus pilosus.*
Variety denomination: 'BURUSIERU'.

BACKGROUND OF THE INVENTION

The new cultivar is a product of a planned breeding program conducted during the summer of 2004 in Miyazaki, Japan. The new variety was discovered in a commercial greenhouse in Miyazaki, Japan by the inventor among a group of seedlings resulting from the self-crossing of the species *Evolvulus pilosus. Evolvulus pilosus* was both the seed and pollen parent. It was discovered by Mr. Akai Nobutaka in October 2004 in Miyazaki, Japan.

Asexual reproduction of the new cultivar 'BURUSIERU' by vegetative cuttings was performed in Miyazaki, Japan and has shown that the unique features of this cultivar are stable and reproduced true to type on successive generations.

SUMMARY OF THE INVENTION

The cultivar 'BURUSIERU' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'BURUSIERU' These characteristics in combination distinguish 'BURUSIERU' as a new and distinct *Evolvulus* cultivar:

1. Short overall plant height.
2. Compact plant habit.
3. Well branched plants.
4. Narrow leaf shape.

Plants of the new cultivar 'BURUSIERU' are similar to plants of the parent variety, *Evolvulus pilosus,* in most horticultural characteristics, however, plants of the new cultivar 'BURUSIERU' differ from the parent variety in the following characteristics:

1. New variety is shorter than parent variety.
2. New variety has shorter internodes than parent variety.

3. New variety has more lateral branches than parent variety.
4. New variety has more acute leaf tips than parent variety.
5. New variety has more narrow leaves than parent variety.

Comparison to existing commercial varieties

Plants of the new cultivar 'BURUSIERU' are similar to plants of the commercial variety, 'Blue Coral,' unpatented in the United States, in most horticultural characteristics, however, plants of the new cultivar 'BURUSIERU' differ from the variety 'Blue Coral' in the following characteristics:

1. Plants of 'BURUSIERU' are shorter than 'Blue Coral.'
2. Internodes of 'BURUSIERU' are shorter than 'Blue Coral.'
3. 'BURUSIERU' has more lateral branches than 'Blue Coral.'

BRIEF DESCRIPTION OF THE PHOTOGRAPH

The accompanying photograph in FIG. 1 illustrates in full color a typical plant with flowers of 'BURUSIERU' grown in a greenhouse. Age of the plant shown is 7 months and the size of the container is 17 cm. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart except where general terms of ordinary dictionary significance are used. The following observations and measurements describe 'BURUSIERU' plants grown in a greenhouse Miyazaki, Japan from January 2006 to July. The growing temperature ranged from 15° C. to 20° C. at night to 23° C. to 25° C. during the day. Measurements and numerical values represent averages of typical flowering types.

Botanical classification: *Evolvulus pilosus* cultivar 'BURUSIERU.'

PROPAGATION

Time to rooting: 20 to 25 days at approximately 25° C.
Root description: Fine, fibrous.

PLANT

Growth habit: Mounding tender perennial.
Height: 20 cm.
Blooming period: April through August.
Plant spread: Approximately 38 cm.
Growth rate: Moderate
Branching characteristics: Very free branching.
Length of lateral branches: Approximately 21.7 cm.
Number of leaves per lateral branch: Approximately 12.
Age of plant described: Approximately 210 days.

FOLIAGE

Leaf:
*Arrangement.*—Alternate.
*Average length.*—Approximately 2.2 cm.
*Average width.*—Approximately 0.7 cm.
*Shape of blade.*—Narrow ovate.
*Apex.*—Acute.
*Base.*—Acute.
*Attachment.*—Stalked.
*Margin.*—Entire.
*Texture of top surface.*—Pubescent.
*Texture of bottom surface.*—Pubescent.
*Leaf internode length.*—Approximately 1.5 cm.
*Color.*—Young foliage upper side: Near R.H.S. Green 137A. Young foliage under side: Near R.H.S. Green 137C. Mature foliage upper side: Near R.H.S. Green 137A. Mature foliage under side: Near R.H.S. 137C.
*Venation.*—Type: Pinnate Venation color upper side: Near R.H.S. Green 137 A. Venation color under side: Near R.H.S. Green 137C.
Petiole:
*Average length.*—Approximately 0.1 cm.
*Color.*—Near R.H.S. Greyed-Purple 183B.
*Diameter.*—Approximately 0.075 cm

FLOWER

Bloom period: Continuous, beginning early Spring through late Summer.
Inflorescence:
*Type.*—Single.
Bud:
*Bud shape.*—Ovate.
*Bud length.*—Approximately 0.5 cm.
*Bud diameter.*—Approximately 0.2 cm.
*Bud color.*—Near R.H.S. Greyed-Orange 177A, base yellow-green; 145C, densely covered with short hairs, average length: 0.75 mm, colored white; Near 155A.
Flower:
*Type.*—Simple, rotate.
*Facing direction.*—Outward to upright.
*Diameter of entire flower.*—Approximately 2 cm.
*Depth of flower.*—Approximately 1.4 cm.
Petals:
*Length of petal.*—Approximately 1.8 cm.
*Width of petal.*—Approximately 1.0 cm.
*Shape of petal.*—Flabellate, lower 85% fused.
*Apex.*—Retuse.
*Petal margin.*—Entire.
Color:
*Upper surface at first opening.*—Near R.H.S. Violet-blue; 96B, base (lower tube) pure white, not on RHS-Color Chart.
*Upper surface at maturity.*—Near R.H.S. Violet-blue; 96B, base (lower tube) pure white, not on RHS-CC.
*Upper surface at fading.*—Not fading.
*Under surface at first opening.*—Near R.H.S. Violet-blue; 96B, fused margins lighter; 92C, base (lower tube) pure white, not on RHS-Color Chart.
*Under surface at maturity.*—Near R.H.S. Violet-blue; 96B, fused margins lighter; 92C, base (lower tube) pure white, not on RHS-Color Chart.
*Under surface at fading.*—Not fading.
Fragrance: None.

SEPAL

Number: 5.
Sepal length: Approximately 0.6 cm.
Sepal width: Approximately 0.1 cm.
Sepal arrangement: Rotate, fused into a campanulate shape, upper 50% free.
Apex shape: Actute.
Margin: Entire.
Color: Inside sepal color near R.H.S. Greyed-orange; 177A, base yellow-green; 145C. Outside sepal color near R.H.S. Greyed-orange; 177A, base yellow-green; 145C.

CALYX

*Calyx shape.*—Campanulate.
*Calyx length.*—0.6 cm.
*Calyx diameter.*—0.4 cm.

PEDUNCLE

No Peduncle Present.

PEDICEL

No Pedicel Present.

REPRODUCTIVE ORGANS

*Number of pistils per flower.*—5.
*Pistil length.*—1.1 cm.
*Stigma shape.*—Linear.
*Stigma color.*—Pure white, not on RHS-Color chart.
*Style color.*—Pure white, not on RHS-Color chart.
*Style length.*—Approximately 0.7 cm.
*Stamens.*—5.
*Anther shape.*—Narrow, oblong.
*Anther color.*—Pure white, not on RHS-Color chart.
*Pollen color.*—Near R.H.S. White 155B.
*Amount of pollen.*—Very low.

OTHER CHARACTERISTICS

Disease resistance: Neither resistance nor susceptibility have been observed.
Drought tolerance and cold tolerance: Observed tolerant of temperatures as low as 5° C. to temperatures as high as 40° C. Drought tolerance has not been observed.
Fruit/Seed production: No seed or fruit observed to date.

What is claimed is:

1. A new and distinct cultivar of *Evolvulus pilosus* plant named 'BURUSIERU' as herein illustrated and described.

* * * * *